United States Patent
Csikós et al.

[11] Patent Number: 5,829,076
[45] Date of Patent: Nov. 3, 1998

[54] X-RAY DIAGNOSTIC APPARATUS WITH TILTABLE PATIENT SUPPORT

[75] Inventors: János Csikós; György Medgyesi, both of Budapest, Hungary

[73] Assignee: U.S. Philips Corporation, New York, N.Y.

[21] Appl. No.: 792,319

[22] Filed: Jan. 31, 1997

[30] Foreign Application Priority Data

Feb. 6, 1996 [DE] Germany .................. 196 05 627.6

[51] Int. Cl.⁶ .................. A61B 6/04; A61G 7/005; A61G 13/00
[52] U.S. Cl. .................. 5/601; 5/610; 378/209
[58] Field of Search .................. 5/601, 610, 600; 378/209

[56] References Cited

U.S. PATENT DOCUMENTS

| | | | |
|---|---|---|---|
| 3,805,080 | 4/1974 | Yager et al. | 5/601 |
| 4,603,845 | 8/1986 | Schmedemann | 5/610 |
| 4,618,133 | 10/1986 | Siczek | 5/601 |
| 4,908,844 | 3/1990 | Masegawa | 5/601 |
| 5,199,123 | 4/1993 | Jacques et al. | 5/601 |
| 5,398,356 | 3/1995 | Pfleger | 5/601 |

FOREIGN PATENT DOCUMENTS

HU207431B  3/1991  Hungary .

*Primary Examiner*—Alexander Grosz
*Attorney, Agent, or Firm*—Jack D. Slobod; Dwight H. Renfrew

[57] ABSTRACT

An X-ray diagnostic apparatus, includes a table underframe and a base unit for supporting the table underframe which can be swiveled about a horizontal axis, and also includes a displacement device for displacing the table underframe relative to the base unit. The device for swiveling the table underframe is usually a complex construction which is expensive to manufacture. Moreover, the supporting therein is often problematic. Therefore, in a simple construction a first point of a guide rod is arranged at a hinge point on the base unit and a second point of the guide rod is arranged at a hinge point on the table underframe, so that a swiveling motion of the table underframe is imposed upon displacement of the table underframe with respect to the base unit.

20 Claims, 6 Drawing Sheets

X-RAY DIAGNOSTIC APPARATUS WITH TILTABLE PATIENT SUPPORT

FIELD OF THE INVENTION

The invention relates to an X-ray diagnostic apparatus, including a table underframe and a base unit for supporting the table underframe which can be swiveled about a horizontal axis, and also including a displacement device for displacing the table underframe relative to the base unit.

DESCRIPTION OF THE RELATED ART

An X-ray diagnostic apparatus of this kind is known from HU-PS 207 431. Therein, the displacement of the table underframe relative to the base unit is realized by a spindle drive. A spindle rotatable about its longitudinal axis is mounted on the table underframe. Via a chain the spindle is driven by a motor mounted on the table underframe. The spindle is engaged by a threaded nut which is mounted, together with a slide block, on the base unit which is connected to the floor. The slide block slides in a guide rail which is mounted on the table underframe so as to extend parallel to the spindle. When the spindle is driven, the table underframe is displaced relative to the base unit. In a further location on the base unit there is mounted a guide roller which rolls on a guide rail mounted on the table underframe. Because of the curvature of this guide rail, a swiveling motion about a horizontal axis is imposed on the table underframe simultaneously with its displacement. To this end, the slide block with the threaded nut is journalled on the base unit in such a manner that it can follow the swiveling motion about the horizontal axis.

The manufacture of the curved guide rail used in the described X-ray diagnostic apparatus is very complex and expensive because only very narrow manufacturing tolerances can be accepted in achieving the desired swiveling motion. The journalling of the slide block on the base unit is also problematic. The major part of the weight permanently bears on the slide block, so that the wear of this bearing is very high. Overall, the construction of the drive is complex and requires a large number of components which must be very accurately manufactured and hence are expensive.

SUMMARY OF THE INVENTION

Therefore, it is an object of the invention to construct an X-ray diagnostic apparatus of the kind set forth in such a manner that the desired swiveling motion is achieved by means of simple, as wear-resistant and as inexpensive components as possible.

According to the invention, this object is achieved in that a first point of a guide rod is arranged at a hinge point on the base unit and a second point of the guide rod is arranged at a hinge point on the table underframe, so that a swiveling motion of the table underframe is imposed upon displacement of the table underframe relative to the base unit.

The swiveling motion of the table underframe is now achieved by means of substantially simpler components. The guide rod is a simple, preferably straight rod which is intended to take up tensile and compressive forces. The guide rod is hinged to the base unit and to the table underframe in such a manner that it can perform a swiveling motion in a plane whereto the horizontal swivel axis of the table underframe extends perpendicularly. Such a hinged attachment can be implemented, for example by way of simple ball bearings.

In the X-ray diagnostic apparatus according to the invention, the table underframe can be swiveled through at least 120°, i.e. from a position in which the table extends vertically (feet down) to a position in which the table has been tilted at least 30° in the other direction with respect to the horizontal position (head down). This enables X-ray imaging of a patient in various positions. The swiveling of the table underframe is uniform and smooth, without abrupt motions.

In an embodiment of the invention the table underframe is provided with a guide rail which slides on a slide block which is hinged to the base unit. A major part of the weight of the apparatus bears on the displacement device. In order to unburden this device, thus minimizing the wear of the displacement device, in this embodiment a major part of the weight is taken up by the slide block. The slide block is journalled on the base unit in such a manner that it can follow the swiveling motion of the table underframe, i.e. that it is swiveled about its longitudinal axis in synchronism with the table underframe.

In order to distribute the weight of the apparatus even better, in a further embodiment of the invention the table underframe is provided with two parallel guide rails and the base unit is provided with two hinged slide blocks on which a respective one of the guide rails slides. The supporting of the table underframe is thus additionally improved and tilting of the table underframe about a horizontal longitudinal axis of the table underframe, extending perpendicularly to the horizontal swivel axis, is prevented.

The apparatus according to the invention is preferably provided with two parallel guide rods, the hinge points on the base unit and on the table underframe always being situated on a common horizontal shaft. The stability of the apparatus during the swiveling motion is thus enhanced. The wear is less because of the distribution of the forces among as many components as possible.

In a preferred embodiment of the invention the displacement device includes a toothed rack which is mounted on the table underframe and a gearwheel which is rotatably mounted on the base unit and engages the toothed rack. The manufacture of these components is very simple and inexpensive. Moreover, the wear of such components is very slight. Replacement of such simple components is also very easy.

In a further preferred embodiment of the invention the displacement device includes two parallel toothed racks which are mounted on the table underframe and two parallel gearwheels which are rotatably journalled on the base unit and each of which engages a respective toothed rack, said gearwheels being mounted on a common drive shaft which is driven by a motor. As a result, the swiveling motion is particularly smooth and uniform.

Alternatively, in a further embodiment of the invention the displacement device includes a spindle which is mounted on the table underframe and a threaded nut which is rotatably journalled on the base unit and engages the spindle. This comparatively simple construction again provides the desired displacement of the table underframe relative to the base unit.

The manufacture is particularly simple and inexpensive in the case of straight components. For example, the guide rails and the toothed racks are constructed so as to be straight and are arranged parallel to one another.

BRIEF DESCRIPTION OF THE DRAWING

The invention will be described in detail hereinafter with reference to the drawing. Therein.

DETAILED DESCRIPTION OF THE PREFERRED EMBODIMENTS

Figure 1:
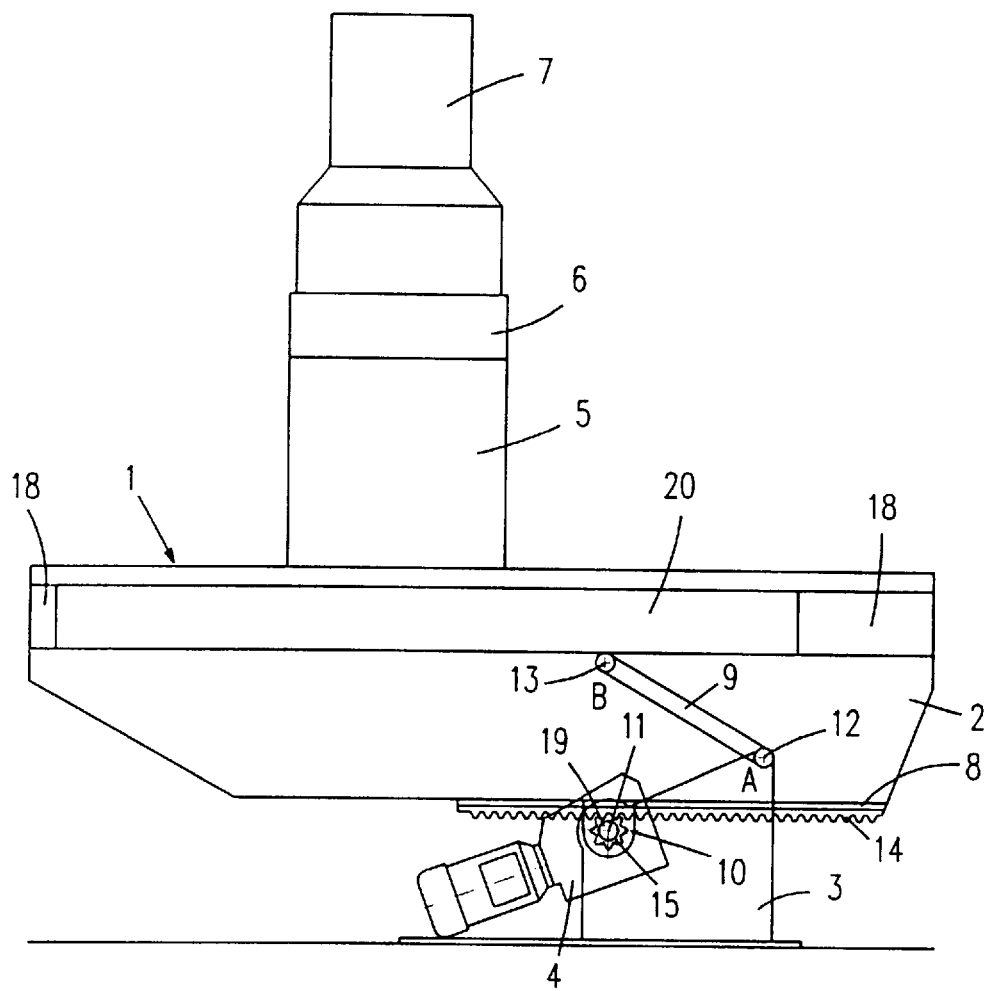
FIG. 1 is a side elevation of an X-ray diagnostic apparatus according to the invention.

The X-ray diagnostic apparatus shown in FIG. 1 includes a table unit 18 with a table top 1 which is mounted so as to be displaceable on a table underframe 2, via a moving grid unit 20. Underneath the table top 1 there is arranged an X-ray tube (not shown) which is mounted on a support 5. Above the table top 1 an X-ray spotfilm device 6 with an image intensifier 7 is mounted on the support 5. Underneath the table top 1 there are situated a base unit 3, connected to the floor, and a motor 4. A drive shaft 19 whose central axis constitutes the axis 11 is arranged to extend perpendicularly to the plane of drawing. The drive shaft 19 is journalled in the base unit 3 and is driven by the motor 4. Two gearwheels 15 are mounted on the drive shaft 19. On the lower side of the table underframe 2 there are arranged two straight, parallel toothed racks 14 which extend parallel to the table top 1. Each of the toothed racks 14 is engaged by a respective one of the gearwheels 15.

Two slide blocks 10 are also mounted on the drive shaft 19. A guide rail 8 which extends parallel to the toothed racks 14 on the lower side of the table underframe 2 slides on each of the slide blocks 10.

The ends of two parallel guide rods 9 are journalled at the hinge points A on a shaft 12, extending parallel to the axis 11, in the base unit 3. The other end of the two guide rods 9 is journalled at the hinge points B on the table underframe 2 on a further shaft 13 extending parallel to the shaft 12, so that the guide rods 9 can be swiveled about the shaft 12 in planes parallel to the plane of drawing.

If the table top 1 is to be moved to another position from the horizontal position shown, for example to the vertical position, the drive shaft 19 with the two gearwheels 15 is driven by the motor 4. The gearwheels 15 engage the toothed racks 14 so that the table underframe 2 is displaced relative to the base unit 3. The table underframe 2 then slides on the slide blocks 10 by way of the guide rails 8. During this displacement the guide rods 9 ensure at the same time that the table underframe 2 is swiveled about a horizontal axis which extends parallel to the axis 11 and changes its position in space. During the swiveling motion of the table underframe 2 the hinge point A of a guide rod 9 moves on a circle of arc around the hinge point B of this guide rod in a plane parallel to the plane of drawing in FIG. 1.

Figure 2:
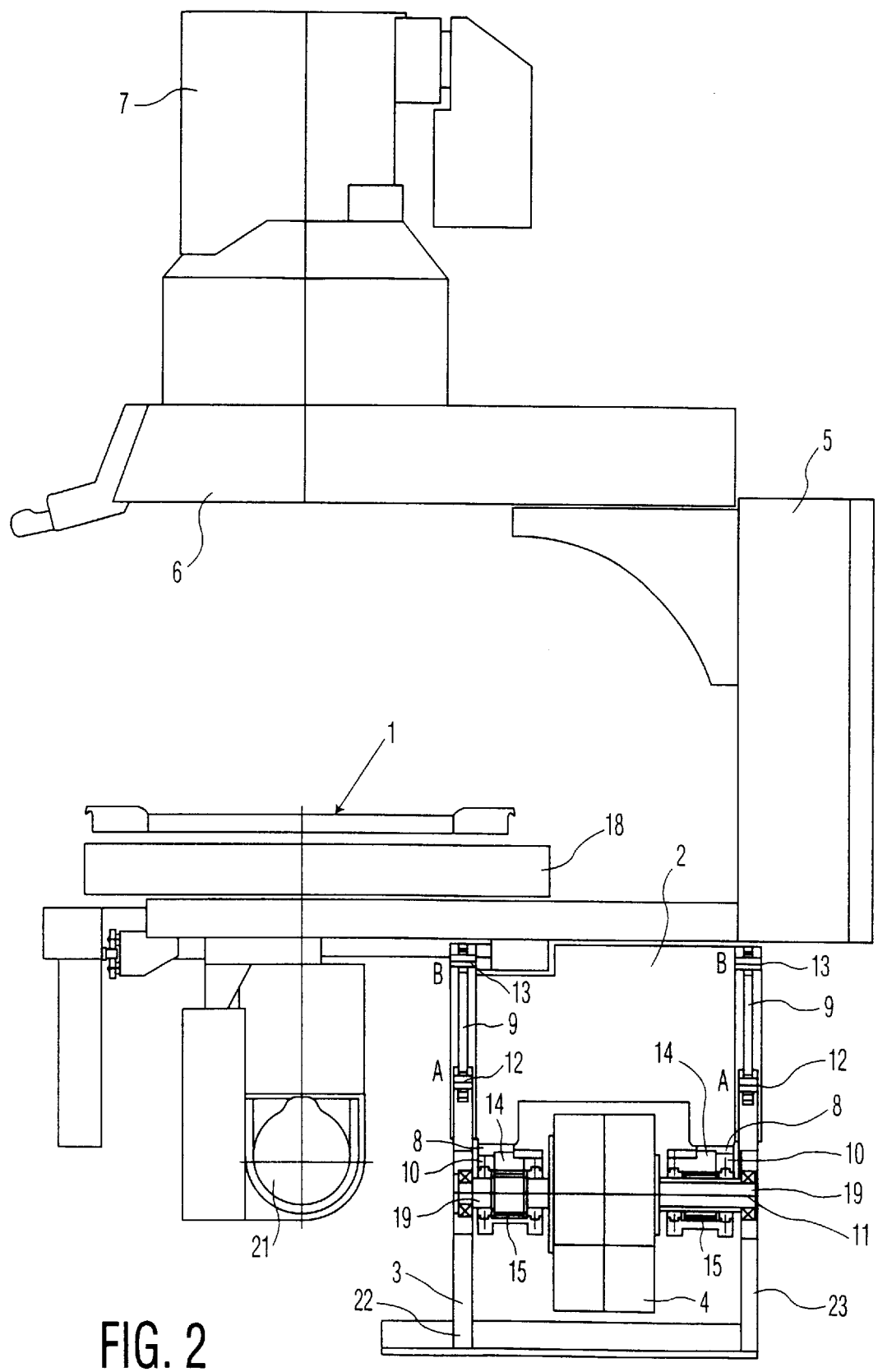
FIG. 2 is a front view of the X-ray diagnostic apparatus shown in FIG. 1.

FIG. 2 is a front view of the X-ray diagnostic apparatus shown in FIG. 1. This Figure shows an X-ray tube 21 which is arranged underneath the table top 1. Adjacent the tube there is situated the table underframe 2 and therebelow the base unit 3 is situated. The base unit 3 includes two vertical walls 22 and 23, for example made of metal, in which the drive shaft 19 is journalled. To both sides of the motor 4 a respective gearwheel 15 is mounted on the drive shaft 19. Moreover, a respective slide block 10 is also arranged on the drive shaft 19 to both sides of the motor 4. The slide blocks 10 are journalled on the drive shaft 19, i.e. they are not rigidly connected to the drive shaft 19, so that they do not follow the rotary driving motion of the drive shaft 19.

Above each slide block 10 a guide rail 8 is provided on the table underframe 2. A toothed rack 14 is rigidly mounted on the table underframe 2 so as to extend partly adjacent and partly underneath each guide rail 8. Above the axis 11 the shaft 12 with the hinge points A of the guide rods 9 extends through the two walls 22 and 23. Above the shaft 12 there is arranged the shaft 13 on which the hinge points B of the guide rods 9 are situated.

Figure 3:
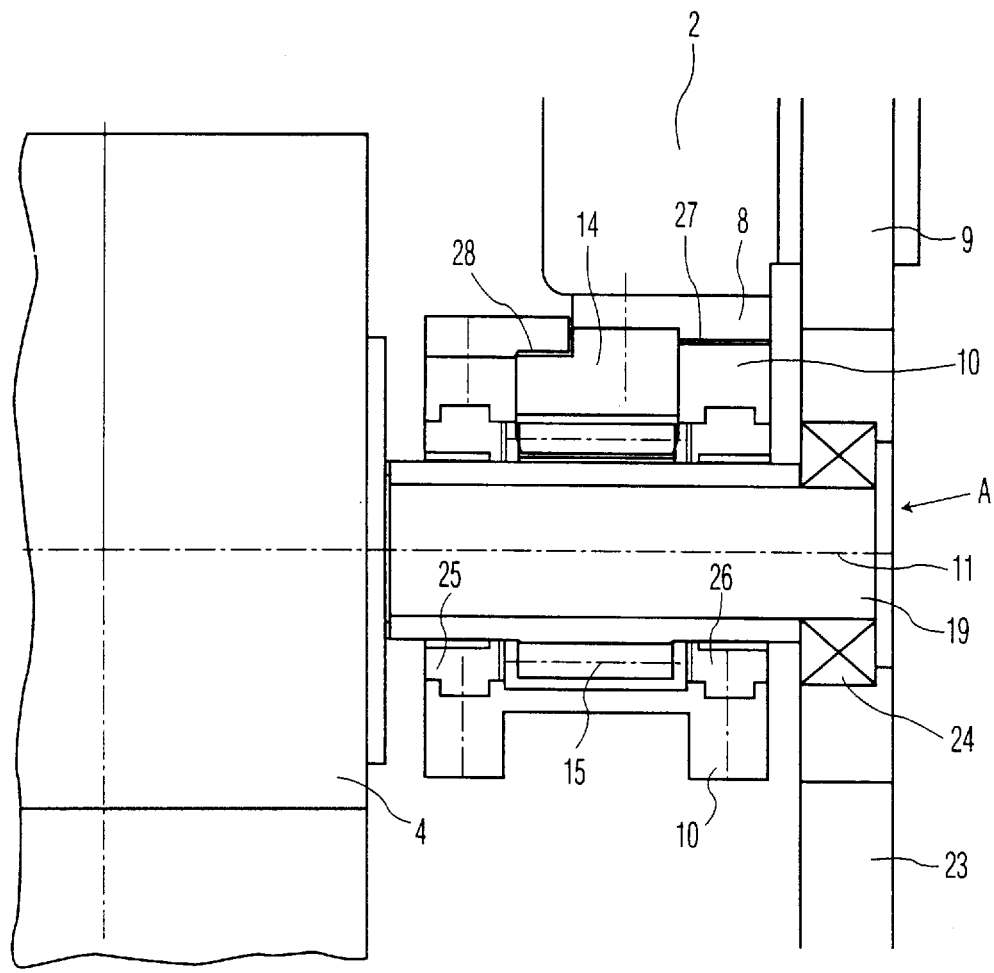
FIG. 3 shows a detail of the apparatus shown in FIG. 2, FIGS. 4 and 5 show the X-ray diagnostic apparatus of FIG. 1 in different positions.

Notably the construction of the slide block 10 will be described hereinafter with reference to the detailed view of FIG. 3. This Figure shows the area around the drive shaft 19 to the right of the motor 4 in FIG. 2. The elements to be described hereinafter are also present to the left of the motor 4 in a practical embodiment, preferably symmetrically relative to the central axis of the motor 4, but have been omitted for the sake of clarity. It is to be noted, however, that the elements shown, situated to one side of the motor 4, would already suffice for suitable operation of the displacement device.

The drive shaft 19 is journalled in the wall 23 of the base unit 3 by way of a bearing 24. The gearwheel 15, rigidly mounted on the drive shaft 19, engages the toothed rack 14. The toothed rack 14 is rigidly connected to a part of the guide rail 8, which itself is rigidly mounted on the table underframe 2. A respective bearing 25, 26 is mounted to each side of the gearwheel 15, the slide block 10 being journalled on said bearings. The guide rail 8 slides on the sliding surface 27 on the slide block 10.

At its side facing the motor 4, a recess is provided in the upper side of the toothed rack 14, which recess is engaged by a part of the slide block 10 so that a sliding surface 28 arises between the slide block 10 and the toothed rack 14.

The slide block 10 and the guide rail 8 serve to take up a major part of the weight of the apparatus and the patient. The X-ray diagnostic apparatus could also be constructed without a guide rail 8 and a slide block 10, but in that case a high degree of wear of the toothed rack 14 and the gearwheel 15 would occur, because these two elements would then have to bear a major part of the weight. In the embodiment shown, the slide block 10 on the sliding surface 27 bears the major part of the weight. Depending on the swiveling position of the table underframe 2, a smaller part of the weight bears on the sliding face 28.

Figure 4:
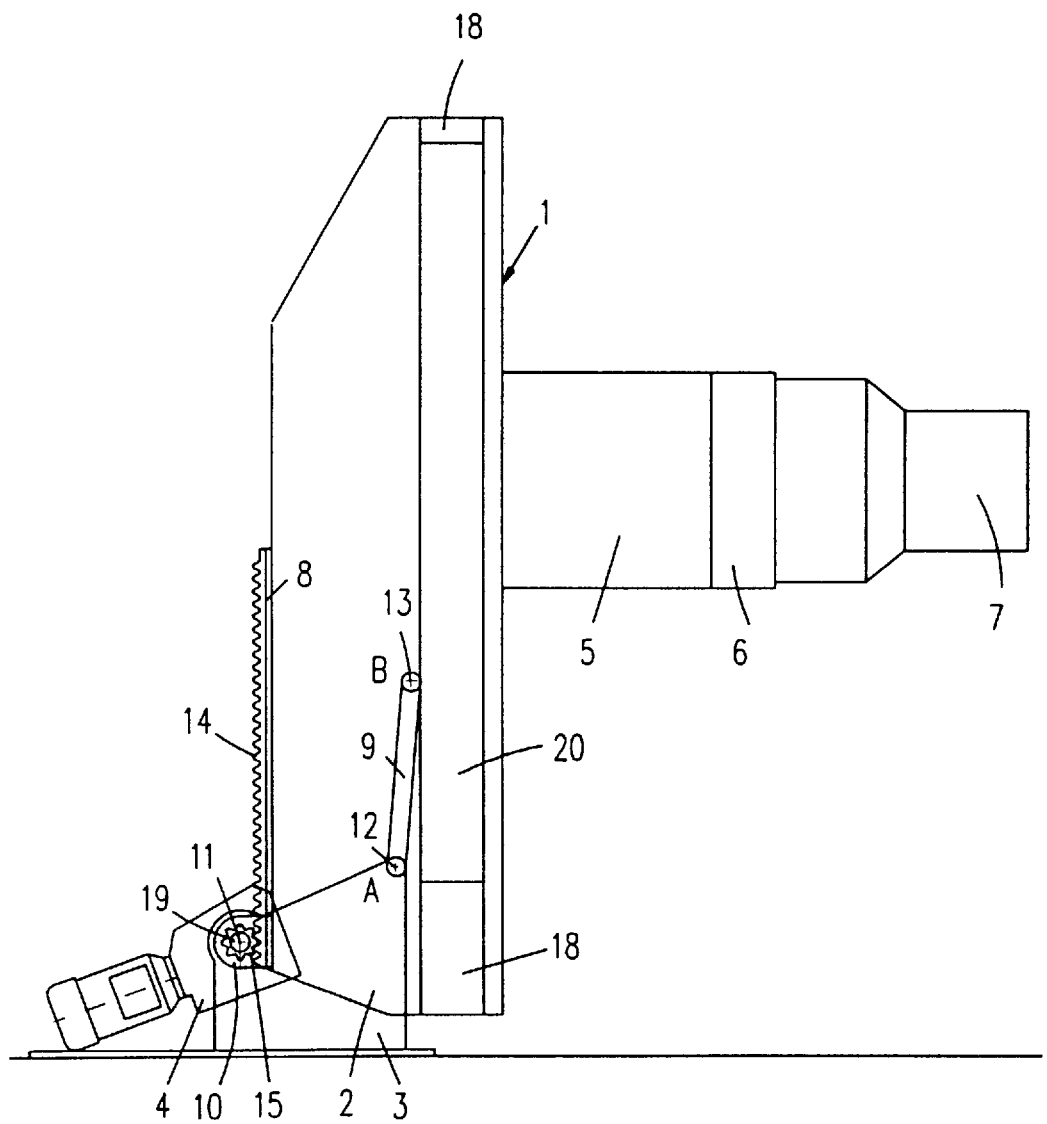

FIG. 4 shows the X-ray diagnostic apparatus according to the invention with the table top 1 in the vertical position (feet down). The gearwheel 15 has now displaced the table underframe 2 with the toothed rack 14 in such a manner that the gearwheel 15 has reached a position at an end of the toothed rack 14. The guide rod 9 has imposed the swiveling of the table underframe 2 and the table top 1 to the vertical position. The guide rod 9 has to take up almost the entire weight in the position shown. A small force acts on the slide block 10 and bears on the sliding face 28 (see FIG. 3).

Figure 5:
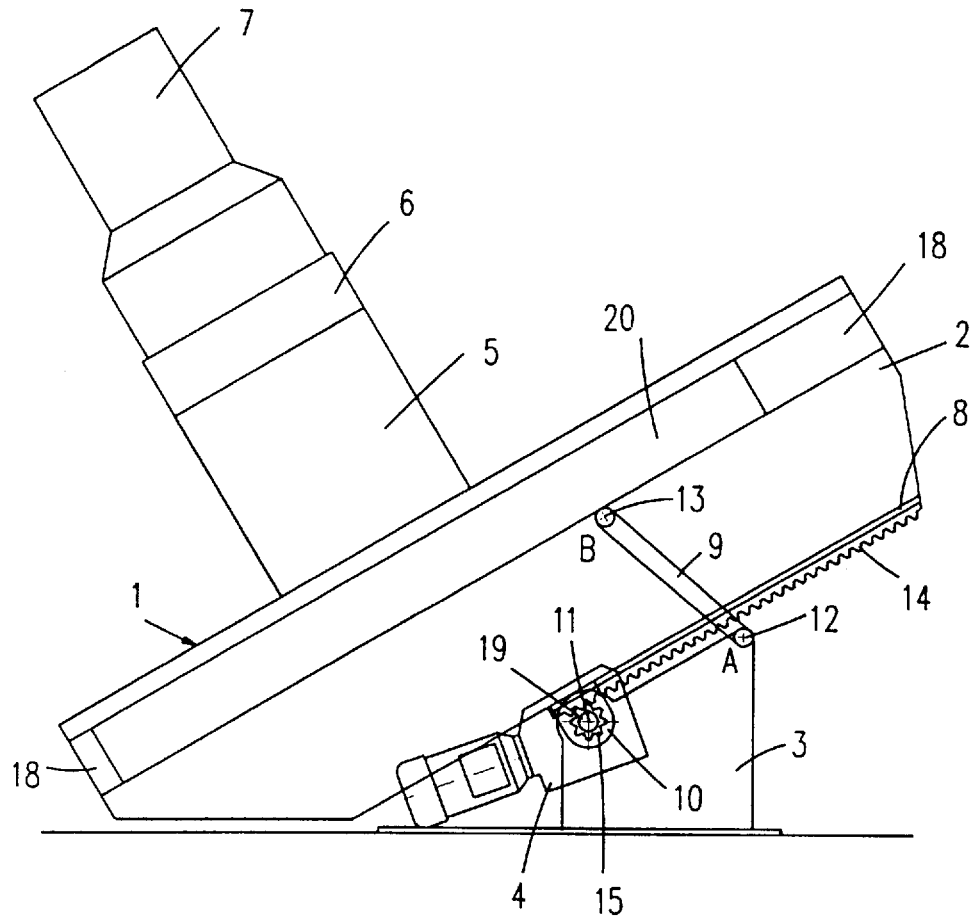

FIG. 5 shows the X-ray diagnostic apparatus in a position in which the table 1 has been swiveled 30° relative to the horizontal position in the opposite direction (head down). In comparison with the position show. in FIG. 4, the gearwheels 15 are then situated at the other end of the toothed racks 14. In order to reach the position shown in FIG. 5 from the position shown in FIG. 4, the table underframe 2 is displaced by means of the gearwheels 15 and the toothed racks 14. The guide rods 9 then move in planes parallel to the plane of drawing. The hinge point B of a guide rod 9 then moves initially counter-clockwise about the shaft 12 until the table 1 reaches the horizontal position. Subsequently, this hinge point B moves clockwise around the shaft 12 until the guide rod 9 reaches the position shown in FIG. 5.

Figure 6:
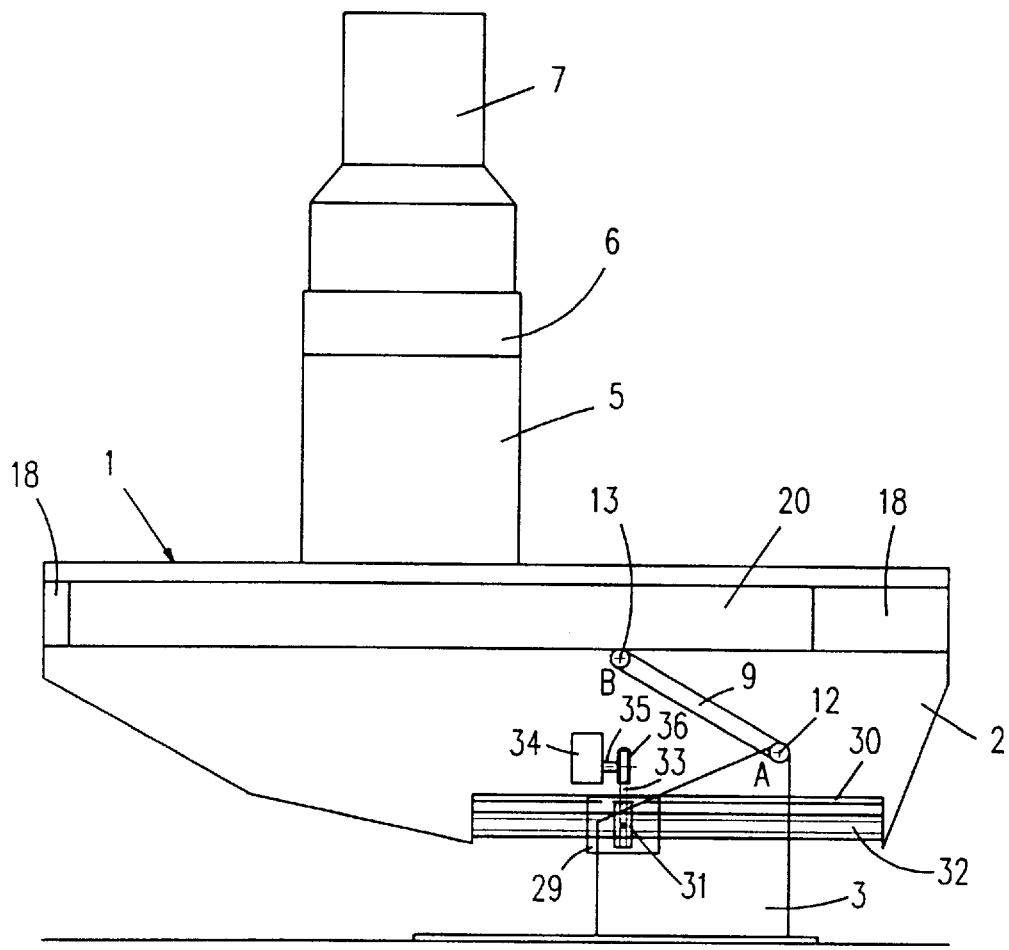
FIG. 6 shows a further embodiment of an X-ray diagnostic apparatus according to the invention with a spindle drive.

FIG. 6 shows an alternative embodiment of an X-ray examination apparatus according to the invention which includes a spindle drive. A slide block 29 is pivotably mounted on the base unit 3, slides in a guide rail 30 provided on the table underframe 2, and is capable of following the swiveling motion of the table underframe 2. The slide block 30 accommodates a threaded nut 31 which engages a spindle 32 which is mounted underneath the guide rail 30 on the table underframe 2 and whose thread matches the thread of the threaded nut 31. The threaded nut 31 is driven, for example via a chain 33, by a shaft 35 with a gearwheel 36, which shaft is driven by a motor 34 and is mounted on the table underframe 2. Upon rotation of the threaded nut 31, the table underframe 2 is displaced relative to the base unit 3 by the spindle 32 because the threaded nut 31 is attached to the base unit 3 together with the slide block 30 and can follow only the swiveling motion of the table underframe 2 but cannot perform a displacement in the horizontal direction. In this embodiment a major part of the weight again bears on the slide block and the guide rail and not on the threaded nut and the spindle, thus reducing the wear of these components.

The guide rods 9 must be constructed so that they are capable of taking up tensile and compressive forces which differ in different positions of the table underframe 2. The position of the shafts 11, 12 and 13 is chosen so that on the one hand a minimum table height is obtained while at the same time adequate clearance underneath the table underframe 2 is ensured for the attending staff or the patient. On the other hand, the forces should be distributed as well as possible among the bearings in order to minimize the wear of components.

In the embodiment shown in FIG. 1, involving a table height of approximately 850 mm, the hinge points A are situated 435 mm above the floor and the hinge points B 625 mm above the floor. The axis 11 extends 255 mm above the floor. The distance between the hinge points A and B amounts approximately 400 mm and the distance between the hinge points A and the axis 11 amounts to approximately 370 mm.

Generally speaking, the part of the displacement device (for example, the toothed rack in FIG. 1) which is mounted on the table underframe is supported on the base unit along only one axis in order to ensure that the table underframe can perform a swiveling motion in addition to the displacement motion. The hinge points A may not be situated in the plane extending perpendicularly to the floor and containing the axis 11. The hinge points B are arranged so that their distance from the floor is greater than the height of the hinge points A.

In the embodiment of the X-ray diagnostic apparatus shown, each time a pair of gearwheels, toothed racks, slide blocks, guide rails and guide rods are provided. In order to achieve the object of the invention, however, this is not necessary. An embodiment would also be feasible in which said elements are provided only in uniquely or in which only the elements which belong together are provided double, for example gearwheel and toothed rack.

For the invention it is not relevant either whether the table underframe is driven by a gearwheel engaging a toothed rack or by a spindle drive. The drive could also be, for example hydraulic. It is merely important that the drive realizes a displacement of the table underframe relative to the base unit.

In an X-ray diagnostic apparatus according to the invention overall a uniform and smooth swiveling motion of the table underframe is achieved, without abrupt motions, throughout a swiveling range of at least 120°.

Moreover, the swiveling of the table underframe is also achieved by means of comparatively simple components which can be inexpensively manufactured. The construction and assembly of the components is very simple, so that the apparatus operates very reliably and requires hardly any maintenance.

We claim:

1. An X-ray diagnostic apparatus comprising a table underframe and a base unit for supporting the table underframe which can be swiveled about a horizontal axis, and also including a displacement device for displacing the table underframe relative to the base unit, characterized in that a first point of a guide rod is arranged at a hinge point (A) on the base unit and a second point of the guide rod is arranged at a hinge point (B) on the table underframe, so that displacement of the table underframe relative to the base unit causes the table underframe to move in a swiveling motion.

2. An X-ray diagnostic apparatus as claimed in claim 1, characterized in that the table underframe is provided with a guide rail which slides on a slide block which is hinged to the base unit.

3. An X-ray diagnostic apparatus as claimed in claim 2, characterized in that the table underframe is provided with two parallel guide rails and the base unit is provided with two hinged slide blocks on which a respective one of the guide rails slides.

4. An X-ray diagnostic apparatus as claimed in claim 3, characterized in that there are provided two parallel guide rods, the hinge points (A, B) on the base unit and on the table underframe, respectively, always being situated on a common horizontal shaft.

5. An X-ray diagnostic apparatus as claimed in claim 4, characterized in that the displacement device includes a toothed rack which is mounted on the table underframe and a gearwheel which is rotatably journalled on the base unit and engages the toothed rack.

6. An X-ray diagnostic apparatus as claimed in claim 3, characterized in that the displacement device includes a toothed rack which is mounted on the table underframe and a gearwheel which is rotatably journalled on the base unit and engages the toothed rack.

7. An X-ray diagnostic apparatus as claimed in claim 2, characterized in that there are provided two parallel guide rods, the hinge points (A, B) on the base unit and on the table underframe, respectively, always being situated on a common horizontal shaft.

8. An X-ray diagnostic apparatus as claimed in claim 7, characterized in that the displacement device includes a toothed rack which is mounted on the table underframe and a gearwheel which is rotatably journalled on the base unit and engages the toothed rack.

9. An X-ray diagnostic apparatus as claimed in claim 2, characterized in that the displacement device includes a toothed rack which is mounted on the table underframe and a gearwheel which is rotatably journalled on the base unit and engages the toothed rack.

10. An X-ray diagnostic apparatus as claimed in claim 2, characterized in that the displacement device includes two parallel toothed racks which are mounted on the table underframe and two parallel gearwheels which are rotatably journalled on the base unit and each of which engages a respective toothed rack, said gearwheels being mounted on a common drive shaft which is driven by a motor.

11. An X-ray diagnostic apparatus as claimed in claim 1, characterized in that the table underframe is provided with two parallel guide rails and the base unit is provided with two hinged slide blocks on which a respective one of the guide rails slides.

12. An X-ray diagnostic apparatus as claimed in claim 11, characterized in that there are provided two parallel guide rods, the hinge points (A, B) on the base unit and on the table underframe, respectively, always being situated on a common horizontal shaft.

13. An X-ray diagnostic apparatus as claimed in claim 12, characterized in that the displacement device includes a toothed rack which is mounted on the table underframe and a gearwheel which is rotatably journalled on the base unit and engages the toothed rack.

14. An X-ray diagnostic apparatus as claimed in claim 11, characterized in that the displacement device includes a toothed rack which is mounted on the table underframe and a gearwheel which is rotatably journalled on the base unit and engages the toothed rack.

15. An X-ray diagnostic apparatus as claimed in claim 11, characterized in that the displacement device includes two parallel toothed racks which are mounted on the table underframe and two parallel gearwheels which are rotatably journalled on the base unit and each of which engages a respective toothed rack, said gearwheels being mounted on a common drive shaft which is driven by a motor.

16. An X-ray diagnostic apparatus as claimed in claim 1, characterized in that there are two parallel guide rods, the hinge points (A, B) on the base unit and on the table underframe, respectively, always being situated on a common horizontal shaft.

17. An X-ray diagnostic apparatus as claimed in claim 16, characterized in that the displacement device includes a toothed rack which is mounted on the table underframe and a gearwheel which is rotatably journalled on the base unit and engages the toothed rack.

18. An X-ray diagnostic apparatus as claimed in claim 1, characterized in that the displacement device includes a toothed rack which is mounted on the table underframe and a gearwheel which is rotatably journalled on the base unit and engages the toothed rack.

19. An X-ray diagnostic apparatus as claimed in claim 1, characterized in that the displacement device includes two parallel toothed racks which are mounted on the table underframe and two parallel gearwheels which are rotatably journalled on the base unit and each of which engages a respective toothed rack, said gearwheels being mounted on a common drive shaft which is driven by a motor.

20. An X-ray diagnostic apparatus as claimed in claim 1, characterized in that the displacement device includes a spindle which is mounted on the table underframe and a threaded nut which is rotatably journalled on the base unit and engages the spindle.

* * * * *